(12) United States Patent
Cheng et al.

(10) Patent No.: US 6,516,218 B1
(45) Date of Patent: Feb. 4, 2003

(54) METHOD FOR DETECTING LEADS OFF IN MULTI-ELECTRODE MEDICAL DIAGNOSTIC SYSTEM

(75) Inventors: Yao-Ming Cheng, Hsinchu (TW); Shin-Dean Kao, Taipei (TW); Ching-Liang Yu, Taoyuan (TW); Teh-Ho Tao, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/494,020

(22) Filed: Jan. 28, 2000

(30) Foreign Application Priority Data

Jun. 30, 1999 (CN) .......................... 88111129 A

(51) Int. Cl.[7] .......................................... A61B 5/0428
(52) U.S. Cl. ...................... 600/509; 600/547; 600/483; 600/513
(58) Field of Search ................. 600/509, 523, 600/547, 483, 513, 484; 128/902, 901

(56) References Cited

U.S. PATENT DOCUMENTS

| 4,494,552 | A | * | 1/1985 | Heath ........................ 128/902 |
| 4,577,639 | A |   | 3/1986 | Simon et al. |
| 4,919,145 | A |   | 4/1990 | Marriott |
| 5,020,541 | A |   | 6/1991 | Marriott |
| 5,042,498 | A | * | 8/1991 | Dukes ........................ 600/509 |
| 5,231,990 | A | * | 8/1993 | Gauglitz ..................... 600/509 |

* cited by examiner

Primary Examiner—Kennedy Schaetzle
(74) Attorney, Agent, or Firm—Kenyon & Kenyon

(57) ABSTRACT

The present invention relates to an apparatus and a method for detecting leads off in a multi-electrode medical diagnostic system. The multi-electrode medical diagnostic system comprises: a carrier circuit unit connected to a plurality of active electrodes and a reference electrode connected to a patient to be detected for generating a plurality of carrier signals of lead impedances and impedance pneumography; a pre-stage protecting circuit coupled to the carrier circuit unit and generating a plurality of input impedance signals to prevent the apparatus from being damaged by defibrillation; and a leads-off detection unit coupled to the carrier circuit unit for demodulating the plurality of input impedance signals into lead impedance related voltages. This present invention further comprises a central processing unit and an analog-to-digital converter for receiving the output of the leads-off detection unit, and calculating the amount and the position of the leads-off, depending on an algorithm embedded in the central processing unit.

3 Claims, 4 Drawing Sheets

METHOD FOR DETECTING LEADS OFF IN MULTI-ELECTRODE MEDICAL DIAGNOSTIC SYSTEM

BACKGROUND OF THIS INVENTION

1. Field of the Invention

The present invention relates to an apparatus and method for detecting leads off in a multi-electrode medical diagnostic system, more particularly to an apparatus and method for detecting leads off in a multi-electrode medical diagnostic system employing the theorem of parallel connecting the input impedances of the leads.

2. Description of the Related Art

Because a multi-electrode medical diagnostic system such as a 5-electrode ECG machine was widely used, it will become an important issue how to detect the connecting condition between all the leads and multi-electrode medical diagnostic system. If leads-off occurs, it will cause the multi-electrode medical diagnostic system to receive wrong or incomplete physiological signals from patients.

A lead includes an electrode and a conductor. A leads-off refers to any lead is separated from a patient's skin and thus a leads-off occurs between the lead and multi-electrode medical diagnostic system. A prior art method for detecting a leads-off between the lead and multi-electrode medical diagnostic system is accomplished by detecting the change in the lead impedance. The impedance includes electrode impedance, conductor impedance and electrode-to-skin connection impedance. When the lead is separated from a patient's skin, a high electrode-to-skin connection impedance would be created. By means of detecting lead impedance, it will be known if the lead is separate from a patient's skin. The prior art measurement method is to apply a dc voltage to every lead through respective loading impedances. When the lead is disconnected from a patent's skin, the output voltage level of an amplifier will be pulled high because the voltage relative to the electrode is separated from the reference, ground. When the output voltage of the amplifier exceeds the threshold value, it means that a leads-off occurs. The above method was disclosed in U.S. Pat No. 4,577,639. However the prior art method in which dc voltage is used will corrupt the patient's physilogical signals especially, the RL lead as a reference ground is disconnected, it will be mistakenly considered that all the leads are disconnected from the patients skin. Another prior art method of detecting a lead disconnection is to use two sets of high frequency carrier signals to detect lead impedance and thoracic impedance, and separating the lead impedance and thoracic impedance by means of demodulating and filtering. When the signal of lead impedance is over the threshold value, it means a leads-off occurs. The above method was disclosed in U.S. Pat. No. 4,919,145 and U.S. Pat. No. 5,020,541. The disadvantage of the method is that only three lead impedance signals (Leads I, Leads II and Leads V) will be measured, so that the correct location in which leads are disconnected is difficult to find out. For example, if the Leads I was disconnected, it is hard to determine that one lead or two leads were disconnected, it is also hard to determine which one of the RA lead or LA lead is connected if only one lead was disconnected. Besides, there is no way to detect whether the RL lead is disconnected.

As above described, the prior art methods do not have an efficient way to detect the correct disconnection location of sole or multiple leads (as U.S. Pat. No. 5,020,541), or to detect if a RL lead is disconnected (as U.S. Pat. No. 5,020,541 and U.S. Pat. No. 4,577,639).

SUMMARY OF THIS INVENTION

The object of the present invention is to resolve the prior art disadvantage of no way to detect the correct disconnection location of a sole or multiple leads, or no way to detect if a RL lead is disconnected. To accomplish the object, this present invention proposes an apparatus that can detect the leads-off, multi-lead ECG and impedance pneumography, and provides a solution to detect the correct disconnection location of the multiple leads and to determine if the RL lead is disconnected. The apparatus of the present invention can inform a physician to recover a fine connection between leads and multi-electrode medical diagnostic system so as to obtain a good quality medical measurement. Furthermore the apparatus of the present invention doesn't have any switch circuit, and thus the complicated circuit control is not needed.

The invention discloses an apparatus for detecting leads-off of multi electrode medical diagnostic system, said apparatus comprising: a carrier circuit unit connected to a plurality of active electrodes and a reference electrode connected to a patient to be detected for generating a plurality of carrier signals of leads and impedance pneumography; a prestage protecting circuit coupled to the carrier circuit unit is to protect the apparatus during defibrillation and generating a plurality of input impedance signals; and a leads-off detection unit coupled to the carrier circuit unit for demodulating the plurality of input impedance signals into lead voltages. This present invention can further comprises a central processing unit and an analog-to-digital converter for receiving the output of the leads-off detection unit, and calculating the amount and the position of lead off situation, depending on an algorithm embedded in the central processing unit.

BRIEF DESCRIPTION OF THE DRAWINGS

The present invention will be described according to the accompanying drawings in which.

PREFERRED EMBODIMENT OF THIS INVENTION

Figure 1:
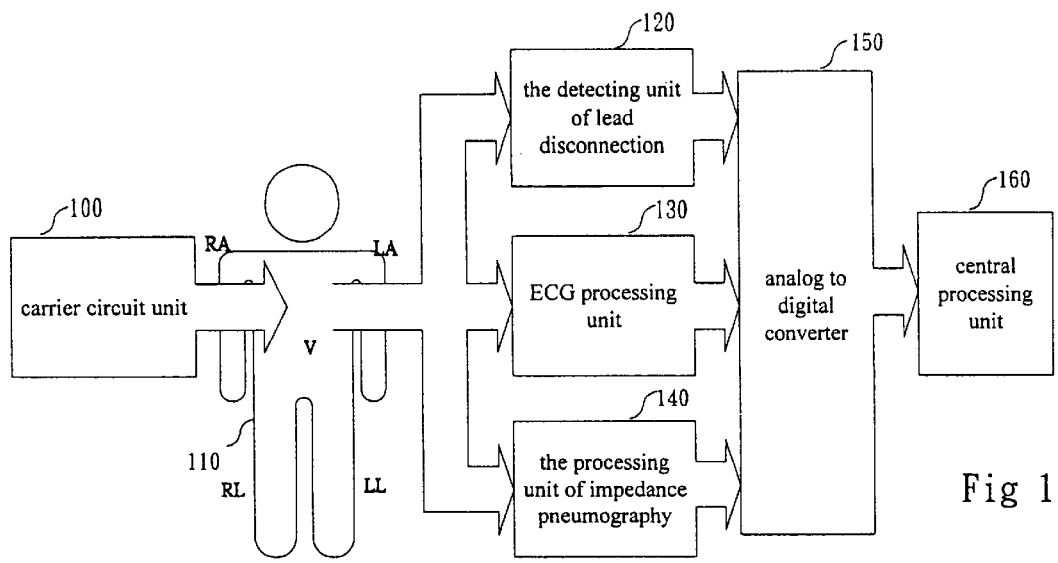
FIG. 1 is a module diagram of a medical diagnostic system.

FIG. 1 is a module diagram of a medical diagnostic system, comprising: a carrier circuit unit 100, used to generate carrier signals for modulating five lead impedances and thoracic impedance and is connected to a patient 110 to be detected; a leads-off detection unit 120, used to demodulate lead input impedances into lead impedance related voltages ($V_{RA}$, $V_{LL}$, $V_{LA}$, $V_V$ and $V_{RL}$); an ECG signal processing unit 130, used to generate signals $V_{ECG1}$ and $V_{ECG2}$ by means of four active electrodes (RA, LL, LA and V) and a reference electrode (RL); a respiration signal processing unit 140, used to demodulate patient thoracic impedance signal into thoracic impedance related voltage ($V_{RESP}$); an analog-to-digital converter 150, used to transfer the analog signals from the leads-off detection unit 120, the ECG signal processing unit 130 and the respiration signal processing unit 140 into digital signals which can be analyzed by a central processing unit 160. The central processing unit defines an algorithm in advance to calculate the Heart Rate (HR), the Respiration Rate (RR) and if any leads disconnected from a multi-electrode medical diagnostic system, and supports the function of dying output waveforms and data transmission.

Figure 2:
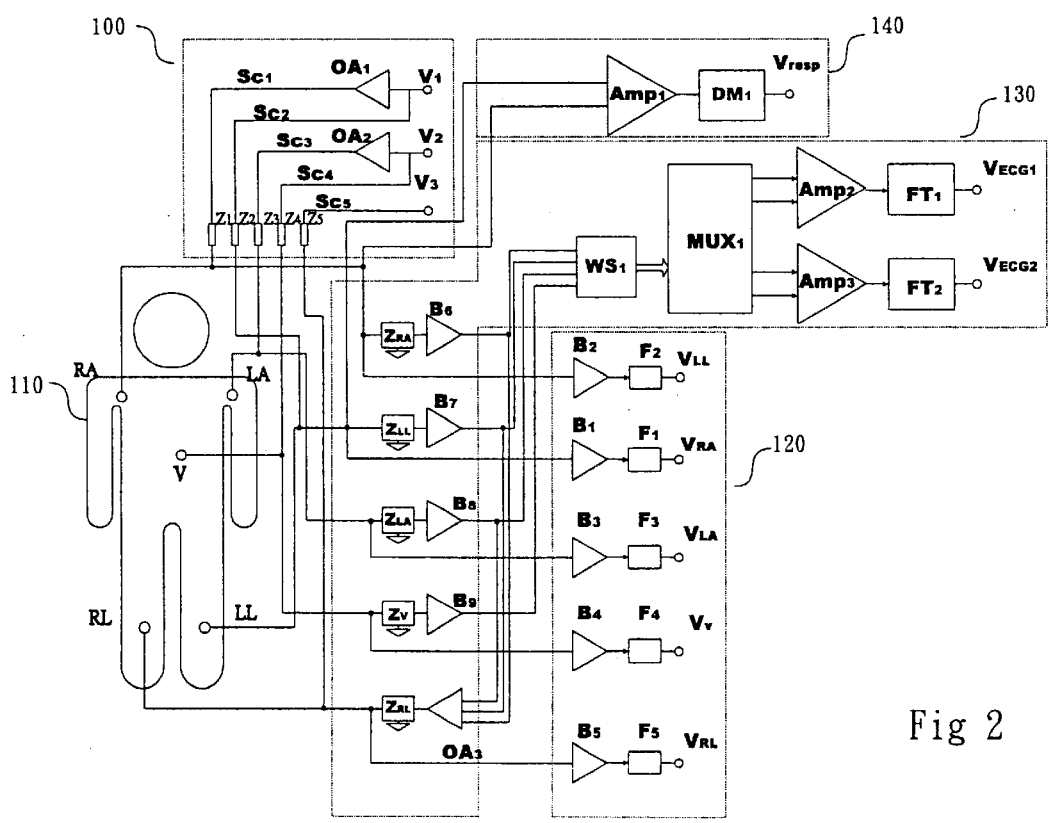
FIG. 2 is a circuit diagram of a medical diagnostic system according to the present invention.

FIG. 2 is a circuit diagram of a medical diagnostic system according to a preferred embodiment to the present invention, wherein four active electrodes (RA, LA, V and LL) and a reference electrode (RL) are used. The electrode RA is connected to the right arm of the patient, the electrode LA connected to the left arm of the patient, the electrode LL connected to the left leg of the patient, the electrode RL connected to the right leg of the patient. The electrode V is connected to a position below the heart of the patient. Usually, the ECG uses multiple active electrodes such as the electrodes RA, LA, V and LL, and provide different aspects of the cardiac activity by different combinations of the active electrodes. For example, the well-known Lead I mode is used to obtain the ECG signal between the electrodes RA and LA, and the well-known Lead II mode is used to obtain the ECG signal between the electrodes RA and LL.

The electrodes RA, LA, V and LL connected to the patient 110 are connected simultaneously to pre-stage protecting circuits $Z_{RA}$, $Z_{LL}$, $Z_V$ and $Z_{RL}$ of the ECG signal processing unit 130. The pre-stage protecting circuits generate lead input impedance signals and mainly used as surge arrestor preventing the apparatus from being defibrillated. The pre-stage protecting circuits have lower impedances at higher frequency and higher input impedances at lower frequency. Such a property is a main fundamental of the present invention. The pre-stage protecting circuits $Z_{RA}$, $Z_{LL}$, $Z_{LA}$ and $Z_V$ are respectively connected to high impedance pre-stage buffers $B_6$, $B_7$, $B_8$ and $B_9$. The pre-stage protecting circuit $Z_{RL}$ is connected to the output of an adder $OA_3$. The adder $OA_3$ is used to calculate the sum of the outputs of the pre-stage buffers $B_6$, $B_7$, $B_8$ and $B_9$ to act as a reference point for reducing noise interference. The outputs of the high impedance pre-stage buffers $B_6$, $B_7$, $B_8$ and $B_9$ are connected to a Wilson bridge $WS_1$ to generate different voltages from different combinations of activity electrodes. The combined voltages are processed by a multiplexer $MUX_1$, two instrument amplifiers $AMP_1$ and $AMP_2$, and two filters $FT_1$ and $FT_2$ to obtain two sets of ECG signals ($V_{ECG1}$, $V_{ECG2}$).

Retrieving impedance respiration signal is accomplished by using high-frequency constant-current impedance carriers provided by the carrier circuit unit 100. A pair of high-frequency opposite-phase carriers passing through impedance $Z_1$, $Z_2$ that limits the current, produces a constant current source. An impedance respiration-modulated signal is extracted from the electrodes RA and LL. The instrument amplifier $AMP_1$ and a demodulating filter circuit $DM_1$ are used to obtain an impedance respiration related voltage $V_{RESP}$ or an impedance pneumography.

The leads-off detection unit 120 has detecting carriers, wherein the electrodes RA and LL use the same carriers $S_{c1}$ and $S_{c2}$ as the impedance respiration. The electrodes V and LA use two carriers $S_{c3}$ and $S_{c4}$ of the same frequency but opposite phases generated by signal source $V_2$ and inverting amplifier $OA_2$. The electrode RL uses a signal source $V_3$ to generate a carrier $S_{c5}$. The purpose of using pairs of carriers with the same frequency but opposite phases is to cooperate with the measurement of impedance respiration signal and to reduce the complexity of the design by means of reducing the amount of signal sources. If an apparatus does not have the function of the impedance pneumography, each carrier can choose different frequencies without affecting the operation of the present invention. The carriers $S_{c1}$, $S_{c2}$, $S_{c3}$, $S_{c4}$ and $S_{c5}$ are transmitted respectively to the electrodes RA, LL, LA, V and RL, and then to pre-stage buffers $B_1$, $B_2$, $B_3$, $B_4$ and $B_5$. The signals from the pre-stage buffers $B_1$, $B_2$, $B_3$, $B_4$ and $B_5$ are demodulated by the lead signal processing circuits $F_1$, $F_2$, $F_3$, $F_4$ and $F_5$ to obtain lead impedance related voltages $V_{RA}$, $V_{LL}$, $V_{LA}$, $V_V$ and $V_{RL}$. The lead signal processing circuits $F_1$, $F_2$, $F_3$, $F_4$ and $F_5$ are composed of a band-pass filter and a peak detector. The central frequency of the bandpass filter corresponds to the frequency of the lead carrier signals. The peak detector does not need a precisely demodulating operation because the change in the signal is obvious after a lead disconnection arises.

Figure 3A:
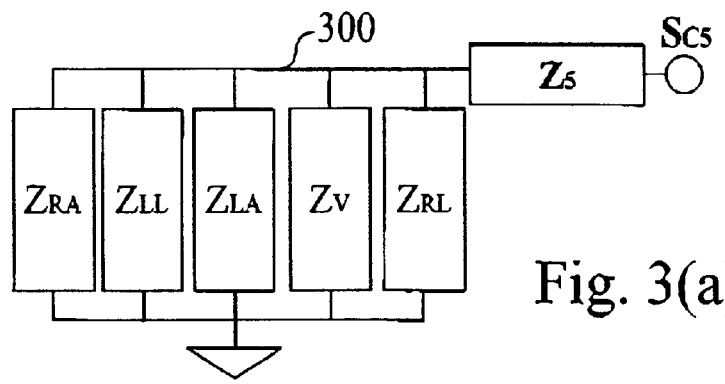
FIG. 3(a) is a schematic diagram of an impedance circuit obtained by using a lead carrier $S_{c5}$, when all leads are connected to a patient to be detected.

FIGS. 3(a)–3(d) are schematic diagrams of various situations of leads-off of the present invention. Because different frequencies or inverse-phase carriers are applied to respectively leads, each lead impedance signal can be analyzed by respectively input carrier signal. FIG. 3(a) is a schematic diagram of an impedance circuit detected by the lead carrier $S_{c5}$, when all the electrodes are connected to the patient. Because the impedance of the person is far less than the lead input impedances in high frequency, the impedance of the patent can be neglected. Thus, a short circuit substantially exists between the leads. When a plurality of resistors are connected in parallel, the resistance becomes small The impedance in FIG. 3(a) is about $1(1/Z_{RA}+1/Z_{LL}+1/Z_{LA}+1/Z_V+1/Z_{RL})$. When $Z_{RA}=Z_{LL}=Z_{LA}=Z_V=Z_{RL}=Z$, the impedance relative to the reference point 300 is about one fifth of the original input impedance. For the reference point 300, the modulated signal will get smaller after the carrier passes through the current-limiting impedance $Z_5$.

Figure 3B:
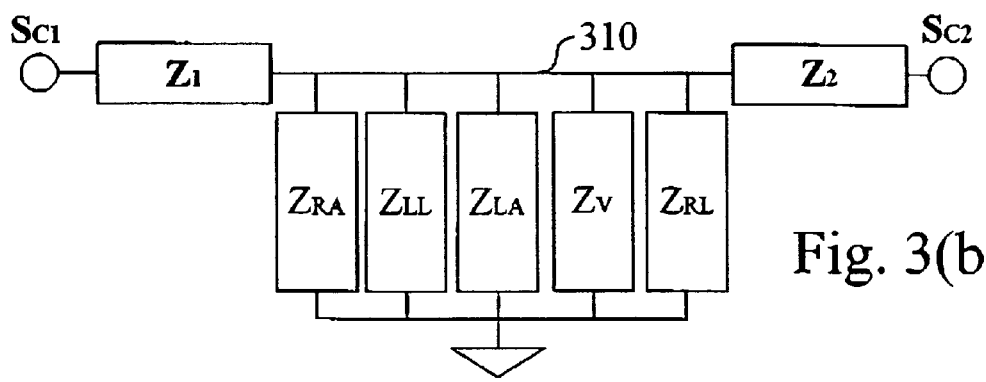
FIG. 3(b) is a schematic diagram of an impedance circuit obtained by using lead carriers $S_{c1}$ and $S_{c2}$ whose frequencies are the same and whose phases are opposite, when all the leads connected to the patient to be detected.

FIG. 3(b) is a schematic diagram of impedance circuit of the present invention, in which an impedance is measured by using the lead carriers $S_{c1}$ and $S_{c2}$ of same frequencies and opposite phases, when all the leads are connected to the patient. Because the carriers have the same frequency and opposite phases, the modulated signal is zero value in an ideal case. In other words, the modulated signal will get smaller if the carriers with the same frequency and opposite phases are coupled to the patient. Because the algorithm of the present invention is based on the detecting mechanism of amplifying a modulated signal after a leads-off occurs, pairs of the carriers with the same frequencies and opposite phases will not effect the operation of the present invention.

Figure 3C:
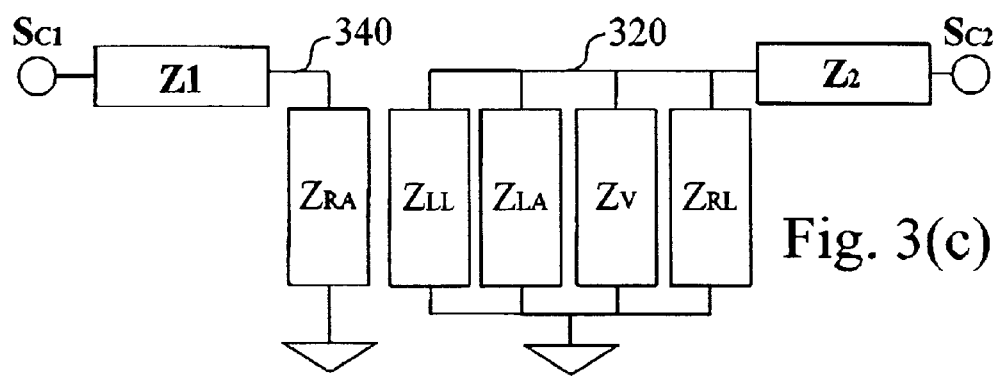
FIG. 3(c) is a schematic diagram of an impedance circuit obtained by using a lead carrier $S_{c2}$, when only the lead RA is disconnected and the other leads are connected to the patient to be detected.

FIG. 3(c) is a schematic diagram of the present invention in which an impedance is measured by using the lead carrier $SC^2$ when only the electrode RA is disconnected and the other leads are connected to the patient. The equivalent impedance relative to the reference point 320 after the impedances $Z_{LL}$, $Z_{LA}$, $Z_V$ and $Z_{RL}$ are connected in parallel is about $1/(1/Z_{LL}+1/Z_{LA}+1/Z_V+1/Z_{RL})$. When $Z_{LL}=Z_{LA}=Z_V=Z_{RL}=Z$, the equivalent impedance is about one fourth of the original input impedance. Similarity, the equivalent impedance relative to the reference point 340 is equal to a single lead input impedance. When two lead disconnections occur, the equivalent impedance is about one third of the original input impedance.

Figure 3D:
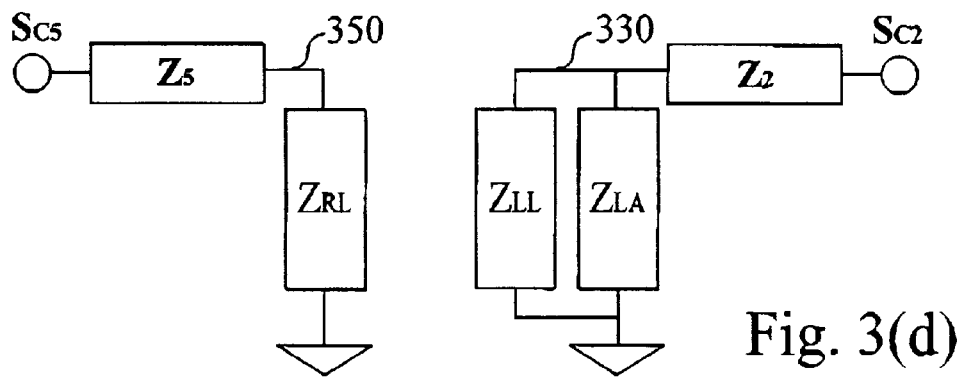
FIG. 3(d) is a schematic diagram of an impedance circuit obtained by using a lead carrier $S_{c2}$, when the leads LL and LA are connected to the patient to be detected.

FIG. 3(d) is a schematic diagram of the present invention in which an impedance is measured by the lead carrier $S_{c2}$ when the electrodes LL and LA are connected to the patient. Using equivalent impedance relative to the reference point 330 is about one half of the original input impedance. Besides, when four leads are disconnected with the patient, the lead carriers will create the maximum modulated signals. As far as five-electrode ECG and impedance pneumography are concerned, in case of four leads off, although the present invention can not detect which leads are disconnected, the situation can be neglected because it is meaningless in practice.

According to the above analysis, when at least 2 leads are connected well, the equivalent impedance will be less than one half of any original impedance. Thus, a threshold voltage can be set up for detecting whether a lead disconnection arises. However, the impedance of the patient is not small enough to be neglected, and the input impedances of all leads are not equal. The threshold voltage can be increased to overcome the nonideal situation, and the tolerance of the difference between input impedances can also be increased. For example, if the threshold voltage is 5/6 times of any original maximal lead impedance related voltage, the tolerance of the difference between any two leads can be increased 5 times. If the threshold voltage is 9/10 times of any original maximal lead impedance related voltage, the tolerance of the difference between any two leads can be increased 9 times. Because noise occurs after the lead impedance modulated, a desired result can not be obtained by infinitely increasing the threshold voltage. Only selecting a suitable threshold voltage can obtain the best detecting result. Besides, the present invention is not limited to five-electrode medical diagnostic system only, but can be applied to multi-electrode ECG system or other medical diagnostic system using detecting electrodes for connecting a patient to be detected. If the quantity of the leads is X, then a total X-2 of the correct location at which the leads are disconnected can be detected. The more of electrodes, the more the benefit is. The number of signal source of the lead carrier is at least X/2, and it will increase the complexity of the circuit design.

Figure 4:
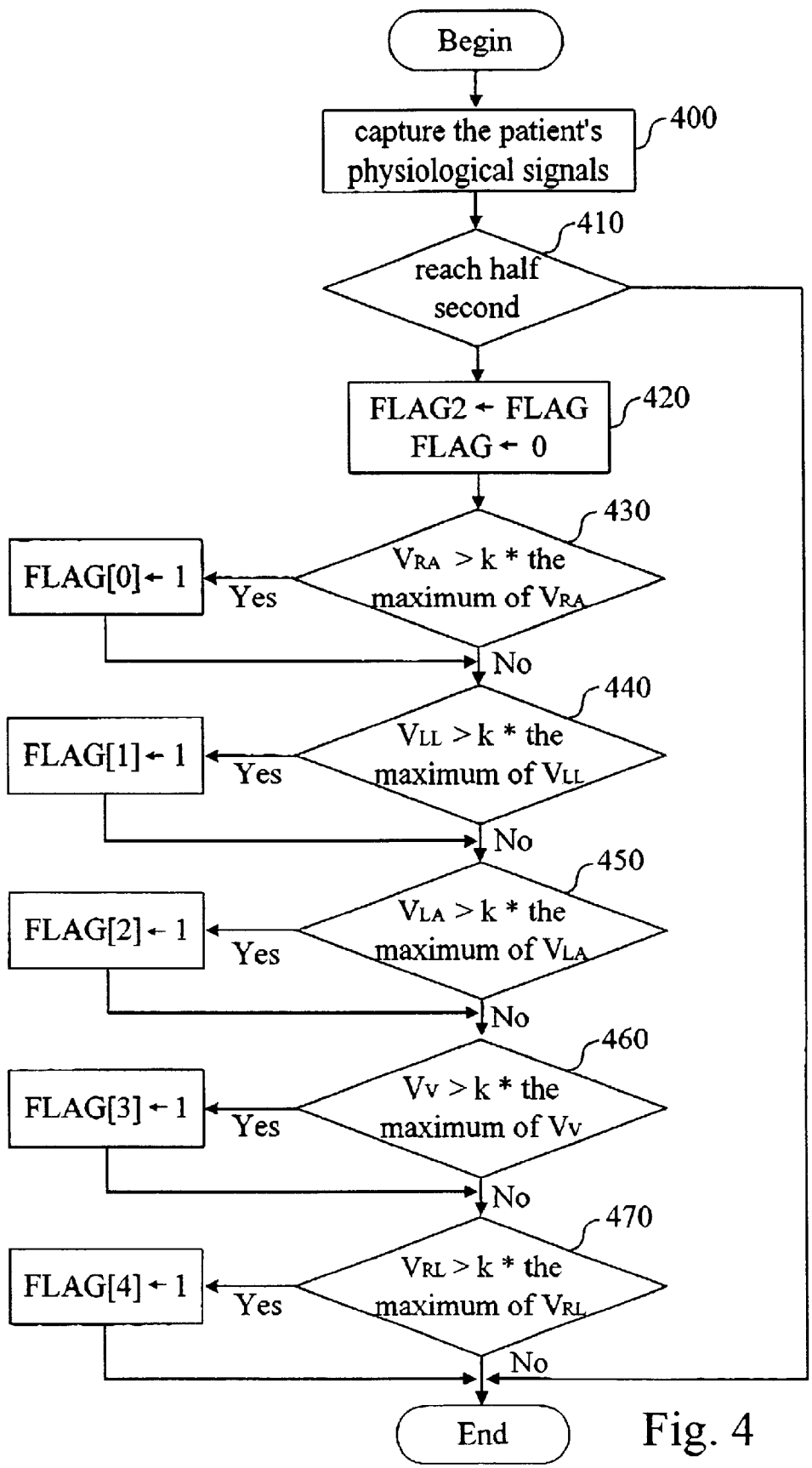
FIG. 4 is a flow diagram of an interrupt program of the present invention for detecting whether leads are disconnected.

FIG. 4 is a flow diagram of an interrupt program for detecting a leads off condition. The interrupt program is triggered by external hardware that captures the ECG and impedance pneumography signals for real-time signal processing. In step 410, the leads-off detection is performed every half a second. If half a second has not passed yet, only in step 400, the ECG and impedance pneumography signals are captured. In step 420, if half a second has passed, a variable stored in a status register "FLAG" will be copied to another status register "FLAG2" to keep the previous result, and all bits for indicating the status of lead connection are cleared. The lead voltages $V_{RA}$, $V_{LL}$, $V_{LA}$, $V_V$ and $V_{RL}$. are sequentially read. If the lead voltages exceed the threshold voltage, i.e, k times the maximal lead impedance related voltage, the lead is considered to be disconnected from the patient, and then a corresponding bit of the register FLAG is set to logic 1. For example, in step 430, whether the electrode RA is disconnected is determined. In step 440, whether the electrode LL is disconnected is determined. In step 450, whether the electrode LA is disconnected is determined. In step 460, whether the electrode V is disconnected is determined. If the lead impedance related voltages do not exceed the threshold voltage, the corresponding bit of the register FLAG remains logic 0 and the execution of the interrupt program is terminated. The interrupt program includes the following algorithm:

if (time_out)
{
  FLAG2←FLAG
  FLAG←0
  if ($V_{RA}$>K·(maximum of $V_{RA}$))
     FLAG[0]←1
  if ($V_{LL}$>K·(maximum of $V_{LL}$))
     FLAG[1]←1
  if ($V_{LA}$>K·(maximum of $V_{LA}$))
     FLAG[2]←1
  ($V_V$>K·(maximum of $V_V$))
     FLAG[3]←1
  if ($V_{RL}$>K·(maximum of $V_{RL}$))
     FLAG[4]←1
  disconnect=FLAG[0]+FLAG[ 1]+FLAG[2]+FLAG[3]+FLAG[4]
}
else exit Wherein k is a threshold value, which varies with different devices, FLAG and FLAG2 are 5-bit status registers; and time—out is a predetermined period for which leads are checked out.

Figure 5:
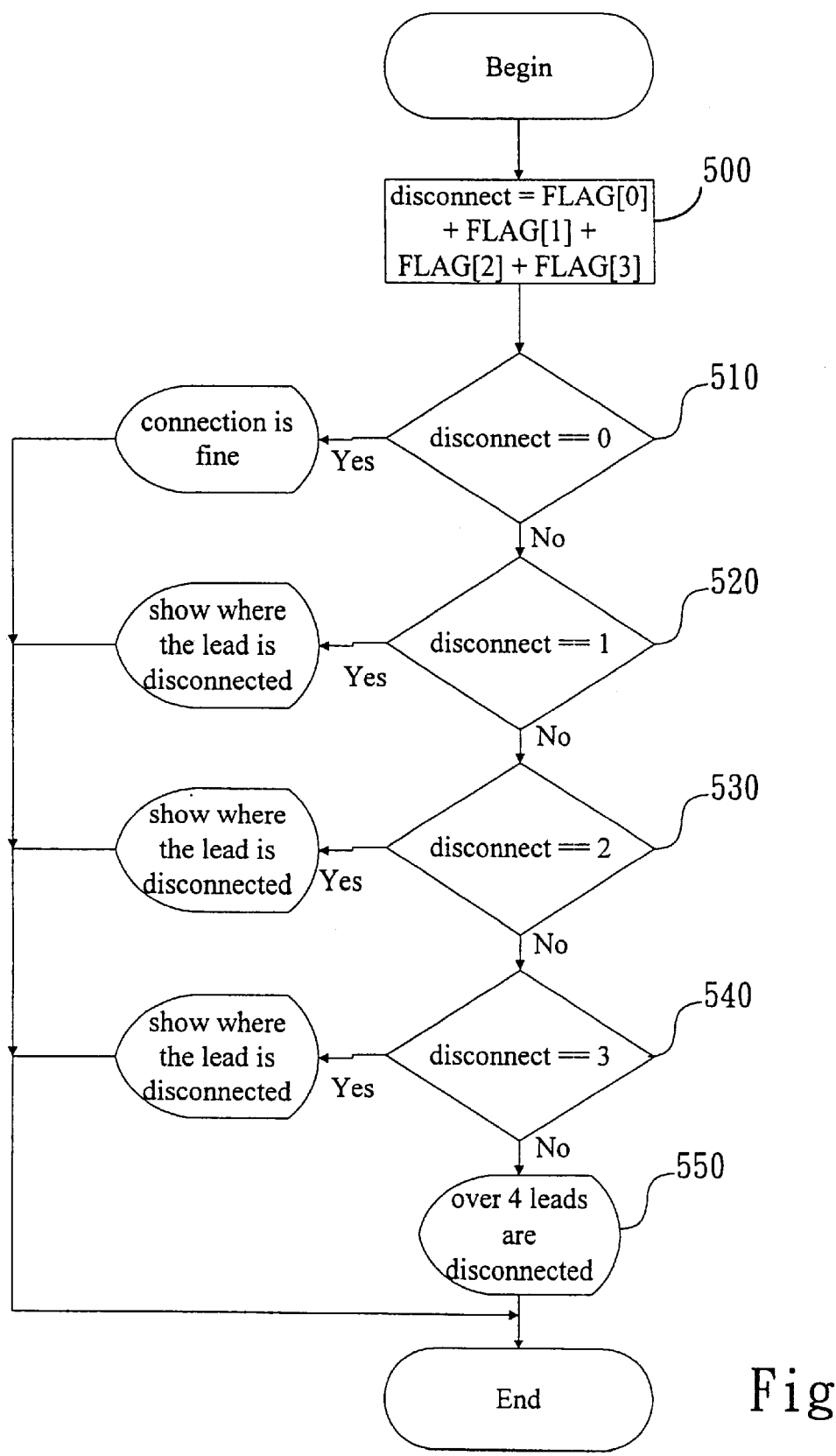
FIG. 5 is a flow diagram of the present invention for analyzing the amount and position of leads that are disconnected.

FIG. 5 is a flow diagram in which the amount and position of leads off are analyzed. Firstly, in step 500, the amount of leads off are summed and the sum is stored in the variable "disconnect." The present invention can detect the situation of three leads off in the five-electrode ECG and impedance pneumography system. The program includes the situation of no lead off (disconnect=0) as in step 510, the situation of one lead off (disconnect=1) as in step 520, the situation of two leads off (disconnect=2) as in step 530, the situation of three leads off (disconnect=3) as in step 540, the situation of more than 4 leads off (disconnect=4) as in step 550. Based on all actual situations, the status register FLAG is analyzed to show corresponding disconnection positions and warning signals. For example, if the voltage $V_{LL}$ is higher than the threshold voltage, the apparatus of the present invention will indicate "lead LL off." If the voltages $V_{RA}$, $V_{LL}$, $V_{LA}$, $V_V$, $V_{RL}$ are bigger than threshold voltage, the apparatus of the present invention will indicate "totally more than four leads off, please check soon" to warn the medical persons to check the connection between the leads and the patient. The analyzing program includes the following algorithm:

if (FLAG[0]==1) print "lead RA off"
if (FLAG[1]==1) print "lead LL off"
if (FLAG[2]==1) print "lead LA off"
if (FLAG[3]==1) print "lead V off"
if (FLAG[4]==1) print "lead RL of"
switch (disconnect)
{
  case '0': print "the connection between leads and patient is fine" break;
  case '1': print "one lead off" break;
  case '2': print "totally two leads off" break;
  case '3': print "totally three leads off" break;
  default: print "totally more than four leads off, please check soon"
}

The above-described embodiments of the present invention are intended to be illustrated only. Numerous alternative embodiments may be devised by those skilled in the art without departing from the scope of the following claims.

What is claimed is:

1. A method for detecting leads off in a multi-electrode medical diagnostic system, said multi-electrode medical diagnostic system comprising a carrier circuit unit connected to a plurality of active electrodes and a reference electrode connected to a patient to be detected; a pre-stage protecting circuit coupled to said carrier circuit unit; and a leads-off detection unit coupled to said carrier circuit unit; said method comprising the following steps:

(1) generating a plurality of carrier signals of lead impedances with opposite phases and impedance pneumography by said carrier circuit unit;

(2) generating a plurality of input impedance signals by said pre-stage protecting circuit to prevent the apparatus from being damaged by defibrillation;

(3) demodulating said plurality of input impedance signals into lead impedance related voltages by said leads-off detection unit;

(4) setting a threshold voltage of said medical diagnostic system;

(5) capturing physiological signals of the patient to be detected;

(6) if a current time reaches a predetermined period for checking whether a leads-off occurs, the following steps will be executed:

(6.1) determining whether the plurality of the lead impedance related voltages are higher than the maximal lead impedance related voltage multiplied by a threshold value;

(6.2) a corresponding bit of a status register is set to logic 1 if any of the plurality of lead impedance related voltages is higher than the maximal lead impedance related voltage multiplied by a threshold value.

2. The method of claim 1, further comprising a first algorithm, executing the following steps:

if (time_out)
   {
      FLAG2←FLAG
      FLAG←0
      if ($V_{RA}$>K·(maximum of $V_{RA}$))
         FLAG[0]←1
      if ($V_{LL}$>K·(maximum of $V_{LL}$))
         FLAG[L]←1
      if ($V_{LA}$>K·(maximum of $V_{LA}$))
         FLAG[2]←1
      if ($V_V$>K·(maximum of $V_V$))
         FLAG[3]←1
      if ($V_{RL}$>K·(maximum of $V_{RL}$))
         FLAG[4]←1
      disconnect=FLAG[0]+FLAG[1]+FLAG[2]+FLAG[3]+FLAG[4]
   }
   else exit.

3. The method of claim 1, further comprising a second algorithm showing the number and position of the leads-off, said second algorithm executing the following steps:

if (FLAG{0}==1)
      print "lead RA off"
   if (FLAG{1}==1)
      print "lead LL off"
   if (FLAG{2}==1)
      print "lead LA off"
   if (FLAG{3}==1)
      print "lead V off"
   if (FLAG{4}==1)
      print "lead RL off"
   switch (disconnect)
   {
      case '0': print "the connection between leads and patient is fine"
         break;
      case '1': print "one lead off"
         break;
      case '2': print "totally two leads off"
         break;
      case '3': print "totally three leads off"
         break;
      default: print "totally more than four leads off, please check soon"
   }.

* * * * *